(12) United States Patent
Yun

(10) Patent No.: US 12,350,014 B2
(45) Date of Patent: Jul. 8, 2025

(54) DENTAL CARIES DIAGNOSTIC DEVICE

(71) Applicant: SAEUM MEDITEC CO., LTD., Bucheon-si (KR)

(72) Inventor: Sang Won Yun, Gwangmyeong-si (KR)

(73) Assignee: SAEUM MEDITEC CO., LTD., Bucheon-si (KR)

( * ) Notice: Subject to any disclaimer, the term of this patent is extended or adjusted under 35 U.S.C. 154(b) by 19 days.

(21) Appl. No.: 17/781,274

(22) PCT Filed: Dec. 2, 2021

(86) PCT No.: PCT/KR2021/018154
§ 371 (c)(1),
(2) Date: May 31, 2022

(87) PCT Pub. No.: WO2023/282409
PCT Pub. Date: Jan. 12, 2023

(65) Prior Publication Data
US 2024/0180427 A1      Jun. 6, 2024

(30) Foreign Application Priority Data
Jul. 6, 2021    (KR) .................. 10-2021-0088513

(51) Int. Cl.
*A61B 5/00*    (2006.01)
(52) U.S. Cl.
CPC .................. *A61B 5/0088* (2013.01)
(58) Field of Classification Search
CPC .................................................. A61B 5/0088
See application file for complete search history.

(56) References Cited

U.S. PATENT DOCUMENTS 4,215,698 A * 8/1980 Nuwayser ............ A61B 5/0534
433/32
4,515,476 A * 5/1985 Ingmar ................. A61B 5/0088
356/417

(Continued)

FOREIGN PATENT DOCUMENTS

DE    202 09 441 U1    9/2002
EP    3 882 839 A1    7/2020

(Continued)

*Primary Examiner* — Cris L. Rodriguez
*Assistant Examiner* — Hao D Mai
(74) *Attorney, Agent, or Firm* — Birch, Stewart, Kolasch & Birch, LLP

(57) ABSTRACT

An optical dental caries diagnostic device can include a body unit, a light-emitting member located in front of the body unit and configured to radiate visible light, and a power supply unit electrically connected to the light-emitting member, where a filter unit detachably coupled to the light-emitting member is provided in front of the light-emitting member. The body unit includes a first body having a first sealed surface and having a hollow cylindrical shape, a second body having a smaller inner diameter than an inner diameter of the first body, a cylindrical connection member having an outer side surface disposed in tight contact with an inner side surface of the first body and an inner side surface located at an outer side surface of the second body, and a control member located in an inner space of the first body.

7 Claims, 3 Drawing Sheets

(a)

(b)

(56) References Cited

U.S. PATENT DOCUMENTS

| | | | | |
|---|---|---|---|---|
| 4,790,751 | A * | 12/1988 | Reinhardt | A61B 1/247 433/140 |
| 5,961,327 | A * | 10/1999 | Lohn | A61B 5/0088 433/29 |
| 6,561,802 | B2 * | 5/2003 | Alexander | A61B 5/0088 433/29 |
| 6,724,522 | B2 * | 4/2004 | Hartung | G02B 6/0011 359/332 |
| 6,764,309 | B2 * | 7/2004 | Cozean | A61N 5/0603 433/29 |
| 8,786,689 | B1 * | 7/2014 | Liu | A61B 1/24 348/68 |
| 2003/0060719 | A1 * | 3/2003 | Irion | A61K 49/0021 600/476 |
| 2005/0003323 | A1 | 1/2005 | Katsuda et al. | |
| 2005/0287490 | A1 * | 12/2005 | Stookey | A61B 1/247 433/29 |
| 2007/0121786 | A1 | 5/2007 | Okawa et al. | |
| 2008/0017787 | A1 | 1/2008 | Okawa et al. | |
| 2008/0082000 | A1 * | 4/2008 | Thoms | A61B 1/00177 600/476 |
| 2008/0160477 | A1 * | 7/2008 | Stookey | A61B 1/015 433/29 |
| 2010/0036260 | A1 | 2/2010 | Zuluaga et al. | |
| 2012/0130254 | A1 * | 5/2012 | Hackel | A61B 5/0088 600/476 |
| 2015/0010878 | A1 * | 1/2015 | Seibel | A61B 5/0071 433/215 |
| 2019/0387976 | A1 | 12/2019 | Pikkula et al. | |

FOREIGN PATENT DOCUMENTS

| | | |
|---|---|---|
| JP | 57-206422 A | 12/1982 |
| JP | 2004-237081 A | 8/2004 |
| JP | 2004-347380 A | 12/2004 |
| JP | 2005-304599 A | 11/2005 |
| JP | 2006-223620 A | 8/2006 |
| JP | 2007-130333 A | 5/2007 |
| JP | 2008-220606 A | 9/2008 |
| JP | 2020-54659 A | 4/2020 |
| KR | 10-0680816 B1 | 2/2007 |
| KR | 10-2007-0027540 A | 3/2007 |
| KR | 10-0800120 B1 | 2/2008 |
| KR | 10-2008-0070112 A | 7/2008 |
| KR | 10-2011-0092738 A | 8/2011 |
| KR | 10-1068462 B1 | 9/2011 |
| KR | 10-1528610 B1 | 6/2015 |
| KR | 10-2016-0041632 A | 4/2016 |
| KR | 20-2016-0001254 U | 4/2016 |
| KR | 10-1618684 B1 | 5/2016 |
| KR | 10-2248141 B1 | 5/2021 |
| KR | 10-2021-0068669 A | 6/2021 |
| WO | WO 2019/131328 A1 | 7/2019 |

* cited by examiner

[FIG. 1]
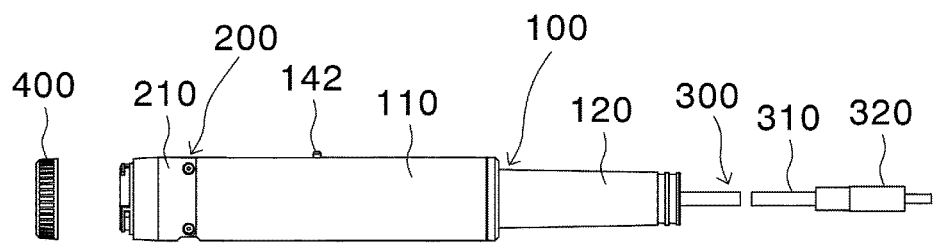
(a)
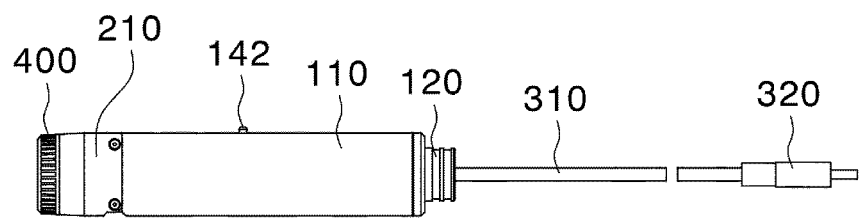
(b)
[FIG. 2]
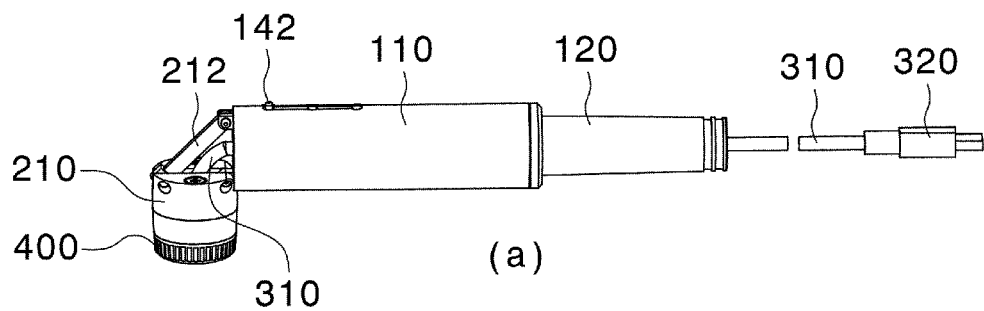
(a)
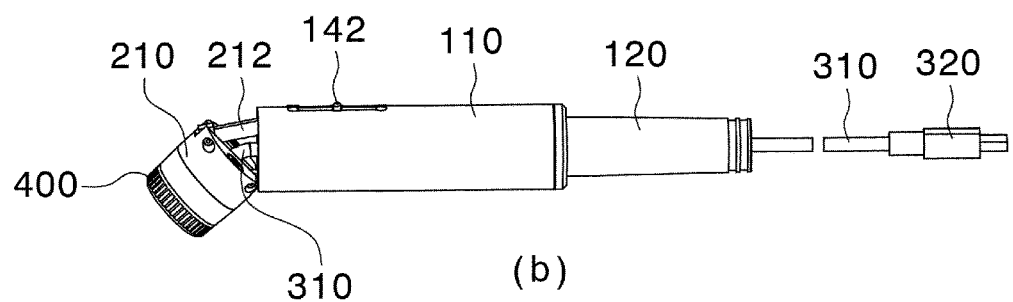
(b)

[FIG. 3]
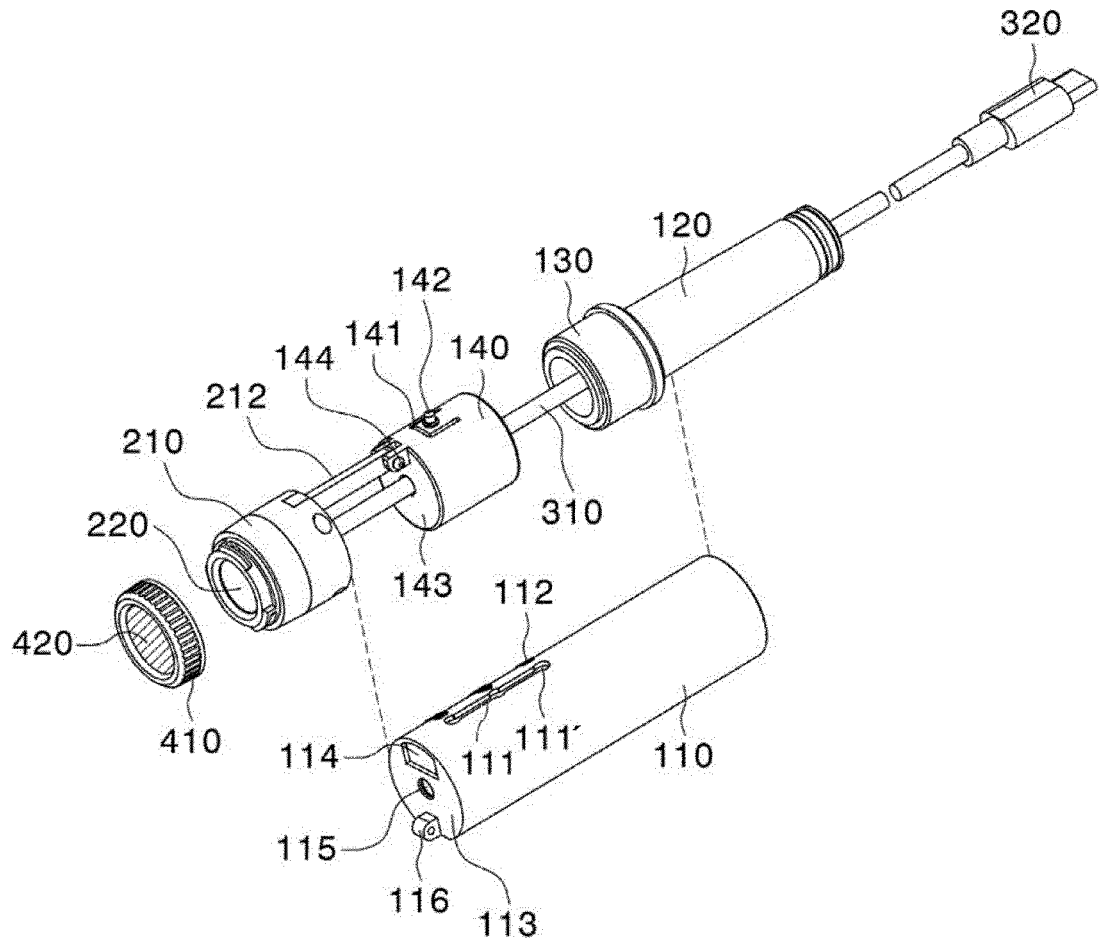
[FIG. 4]
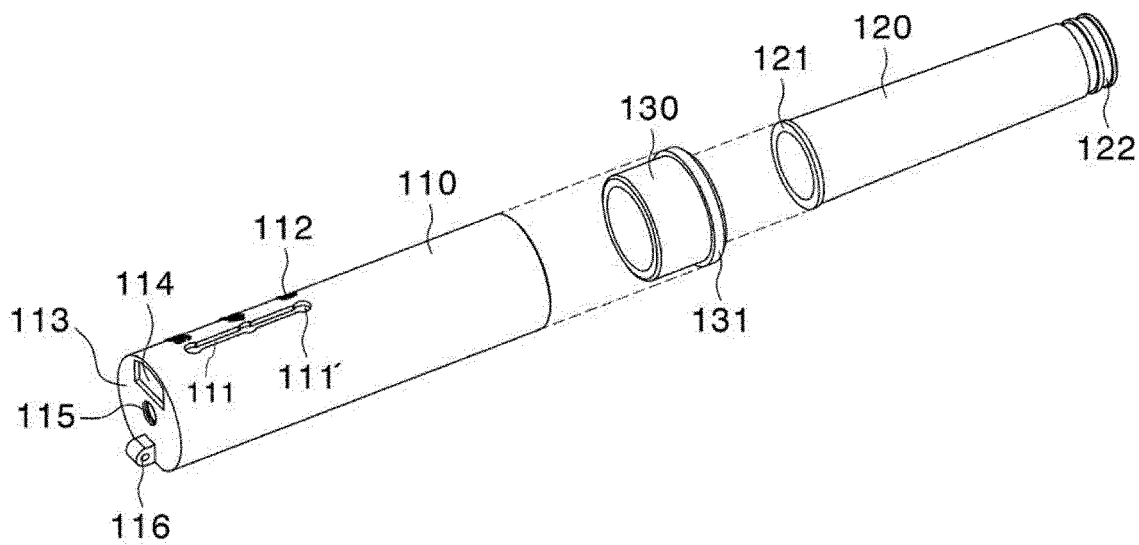

【FIG. 5】
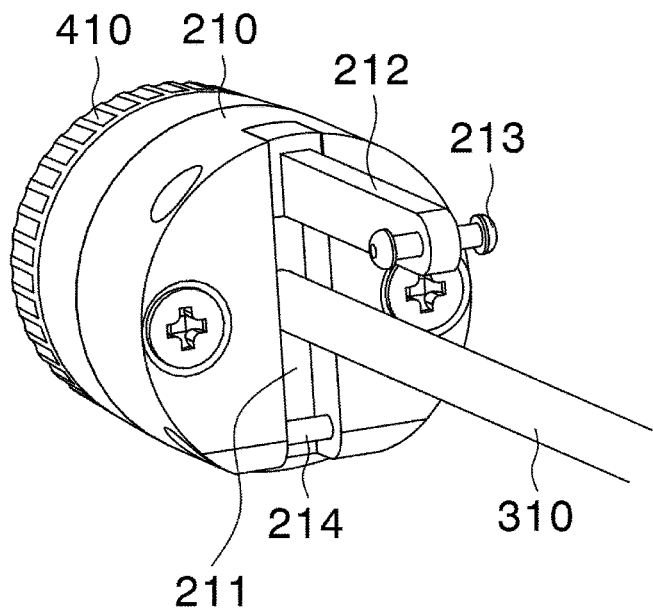
【FIG. 6】
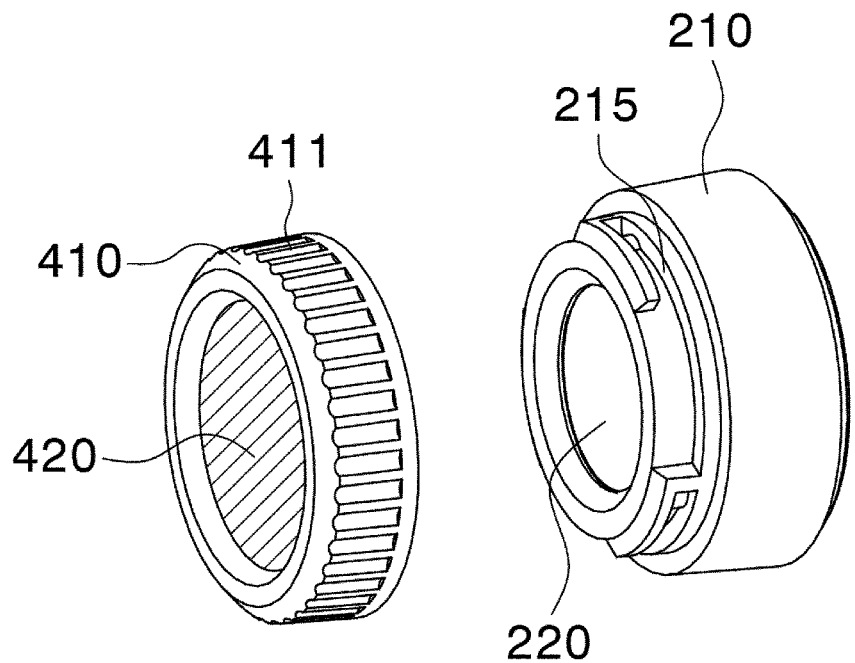

DENTAL CARIES DIAGNOSTIC DEVICE

TECHNICAL FIELD

This application is the National Phase of PCT International Application No. PCT/KR2021/018154, filed on Dec. 2, 2021, which claims priority under 35 U.S.C. 119 (a) to Patent Application No. 10-2021-0088513, filed in Republic of Korea on Jul. 6, 2021, all of these applications are hereby expressly incorporated by reference into the present application.

The present invention relates to a dental caries diagnostic device. More particularly, the present invention relates to an optical dental caries diagnostic device capable of radiating light to easily check whether dental caries occurs and furthermore capable of being very conveniently used and stored.

BACKGROUND ART

Dental caries (decayed teeth) and gum diseases (gingivitis and periodontitis) are the world's most common chronic diseases; however, most people do not recognize such diseases as chronic diseases.

Dental caries and gum diseases progress through different processes; however, causes thereof are the same, i.e. dental plaque. Dental caries and gum diseases may get worse due to genetic characteristics of people or their own diseases, but it is known that a clinical fundamental cause of dental caries and gum diseases is dental plaque.

In particular, it is known that gum diseases, which are social diseases having high prevalence, affect cardiovascular disease as well as premature loss of teeth. Dental plaque is one of the main causes of periodontal tissue disease. If dental plaque is not properly treated, therefore, the dental plaque continuously accumulates, and periodontal tissues are chronically stimulated, whereby the periodontal tissues are inflamed.

Consequently, bad oral health may have a negative influence on development of children's mouths, and may cause many children to miss class for about 50 million hours every year. In addition, oral health affects confidence and social skills of children and their potential for success after growth. That is, oral health is essential to overall health and well-being of children.

Korean Registered Patent No. 2248141, which is prior art for diagnosing whether dental caries occur, discloses a pen light for dental disease diagnosis includes a pen type body unit formed so as to be long in a longitudinal direction such that a user can hold the body unit and a light emission unit provided at a tip end of the body unit, the light emission unit being configured to radiate light having a predetermined wavelength in the longitudinal direction, wherein the light emission unit is an LED, and the wavelength of the light radiated by the light emission unit is set to a wavelength ranging from 402.2 nm to 404.0 nm such that bacterial metabolites existing at a lesion have characteristics of absorbing the wavelength of the light that has been transmitted through teeth under environmental conditions in which at least one of intraoral plaque, tartar, and debris exists and such that caries formed in enamel of the teeth, caries formed in cementum of the teeth, caries formed in enamel and dentine of the teeth, and caries formed in enamel and dentine of the teeth, are all discolored to a reaction color in order to check the position, range, and depth of the caries.

According to the above prior art, the pen light is portable and is capable of determining whether caries occurs. However, an LED capable of radiating only light having a wavelength of 402.2 nm to 404.0 nm is required, whereby manufacturing cost is increased. Furthermore, the pen light is of a long pen type, and therefore it is inconvenient to store the pen light. In addition, caries occurs not only at front surfaces of the teeth but also at rear surfaces of the teeth; however, it is very inconvenient to check whether caries occurs at the rear surfaces of the teeth.

PRIOR ART DOCUMENT (Patent Document 1) Korean Registered Patent No.

DISCLOSURE

Technical Problem

The present invention has been made in view of the above problems, and it is an object of the present invention to provide an optical dental caries diagnostic device capable of being manufactured at low manufacturing cost and capable of being easily used and stored.

It is another object of the present invention to provide an optical dental caries diagnostic device capable of sufficiently radiating light even to recessed portions of teeth, to which light is not sufficiently radiated, such as rear surfaces of the teeth, as well as front surfaces of the teeth.

Technical Solution

An optical dental caries diagnostic device according to the present invention to accomplish the above objects includes a body unit (100) having a predetermined length; a light-emitting member (200) located in front of the body unit (100); the light-emitting member being configured to radiate visible light, and a power supply unit (300) electrically connected to the light-emitting member (200), the power supply unit extending through the body unit (100) and then being exposed at a rear of the body unit (100), wherein a filter unit (400) detachably coupled to the light-emitting member (200) is provided in front of the light-emitting member (200).

Also, in the optical dental caries diagnostic device according to the present invention, the filter unit (400) may include a filter frame (410) formed in a cylindrical shape having a predetermined length, the filter frame being provided at an outer side surface thereof with a second concavo-convex portion (411), and an optical filter (420) mounted to the filter frame (410), the optical filter being configured to selectively transmit only light having a wavelength band of 405 to 410 nm.

Also, in the optical dental caries diagnostic device according to the present invention, the light-emitting member (200) may be connected to the body unit (100) so as to be turnable at a predetermined angle therefrom.

Also, in the optical dental caries diagnostic device according to the present invention, the length of the body unit (100) may be adjustable.

Also, in the optical dental caries diagnostic device according to the present invention, the body unit (100) may include a first body (110) having a first sealed surface provided at an end of one side thereof, the first body having a hollow cylindrical shape, a second body (120) having a smaller inner diameter than the first body (110), the second body being formed in a cylindrical shape having open opposite ends and an empty interior, a cylindrical connection member (130) having an outer side surface disposed in tight contact with an inner surface of an edge of the outer side of the first body (110) and an inner side surface located at an outer surface of the second body (120), and a control member (140) located in an inner space of an edge of the one side of the first body (110), the control member being configured to control turning of the light-emitting member (200).

Also, in the optical dental caries diagnostic device according to the present invention, the first body (110) may include a slit (111) formed in a circumferential surface thereof in a longitudinal direction thereof, an indicator (112) provided in the vicinity of the slit (111); a first through-hole (114) formed in the first sealed surface (113), a second through-hole (115) formed in the first sealed surface (113), and a first fastening protrusion (116) formed on an outside of the first sealed surface (113), the second body (120) may include a first flange (121) provided at an outer side surface of an edge of one side thereof and a first concavo-convex portion (122) provided at an outer side surface of an edge of the other side thereof, the connection member (130) may include a second flange (131) provided at an outer side surface of an edge of the other side thereof, the control member (140) may have a hollow cylindrical shape, the control member including an incised portion (141) provided at a predetermined position of a circumferential surface thereof, a projecting portion (142) provided in the vicinity of the incised portion (141), and a second fastening protrusion (144) provided at an end of one side thereof so as to protrude therefrom by a predetermined length, and the light-emitting member (200) may include a lamp frame (210), and a lamp (220) mounted to the lamp frame (210), the lamp frame (210) having a cylindrical shape, the lamp frame being located in front of the first sealed surface (113) of the first body (110), the lamp frame including an incised groove (211) formed in an end surface of one side thereof facing the first sealed surface (113), the incised groove extending through a central point thereof while having a predetermined width, a hinge shaft (212) having one side connected to the incised groove (211) and the other side connected to the second fastening protrusion (144), and a second fastening member (214) configured to connect the first fastening protrusion (116) of the first body (110) and the lamp frame (210) to each other.

Also, in the optical dental caries diagnostic device according to the present invention, the lamp frame (210) may be provided at a predetermined position of an outer side surface thereof with a coupling groove (215) configured to fix the filter frame (410).

Also, in the optical dental caries diagnostic device according to the present invention, the power supply unit (300) may include a cable (310) having a predetermined length and a connection terminal (320) provided at an end of one side of the cable (310), the connection terminal (320) being of a type capable of being connected to a portable electronic device and a non-portable electronic device.

Advantageous Effects

An optical dental caries diagnostic device according to the present invention has an advantage in that a filter configured to selectively transmit only light having a specific wavelength band is provided in front of a light-emitting member so as to be detachably attached thereto, whereby it is possible to reduce lamp purchase cost.

In addition, the optical dental caries diagnostic device according to the present invention has a merit in that the length of a body unit configured to be gripped by the hand is adjustable, whereby it is possible to conveniently use the optical dental caries diagnostic device and to easily store the optical dental caries diagnostic device.

Furthermore, the optical dental caries diagnostic device according to the present invention has an advantage in that the light-emitting member is configured to be bendable at a predetermined angle, whereby it is possible to easily check whether dental caries occur at rear surfaces of teeth.

DESCRIPTION OF DRAWINGS

FIG. 1 is a front view of an optical dental caries diagnostic device according to the present invention, wherein (a) of FIG. 1 shows the state in which the length of a body unit is increased and (b) of FIG. 1 shows the state in which the length of the body unit is decreased.

FIG. 2 is a front view of the optical dental caries diagnostic device according to the present invention, wherein (a) of FIG. 2 shows the state in which a light-emitting member is bent at a right angle and (b) of FIG. 2 shows the state in which the light-emitting member is bent at 45 degrees.

FIG. 3 is an exploded perspective view of the optical dental caries diagnostic device according to the present invention.

FIG. 4 is an exploded perspective view of the body unit constituting the optical dental caries diagnostic device according to the present invention.

FIG. 5 is a perspective view of the light-emitting member constituting the optical dental caries diagnostic device according to the present invention when viewed from a rear side thereof.

FIG. 6 is a perspective view illustrating an attachment and detachment structure of a filter unit constituting the optical dental caries diagnostic device according to the present invention.

BEST MODE

In the present application, it should be understood that the terms "comprises," "has," "includes," etc., when used in this specification, specify the presence of stated features, numbers, steps, operations, elements, components, or combinations thereof, but do not preclude the presence or addition of one or more other features, numbers, steps, operations, elements, components, or combinations thereof.

It will be understood that, when a component is referred to as being "connected to" or "coupled to" another component, it may be directly connected to or coupled to the other component, or intervening components may be present. In contrast, when a component is referred to as being "directly connected to" or "directly coupled to" another component, there are no intervening components present. Other terms that describe the relationship between components, such as "between" and "directly between" or "adjacent to" and "directly adjacent to", must be interpreted in the same manner.

Unless otherwise defined, all terms, including technical and scientific terms, used in this specification have the same meanings as those commonly understood by a person having ordinary skill in the art to which the present invention pertains. It will be further understood that terms, such as those defined in commonly used dictionaries, should be interpreted as having meanings consistent with their meanings in the context of the relevant art and the present disclosure, and are not to be interpreted in an idealized or overly formal sense unless expressly so defined herein.

Hereinafter, an optical dental caries diagnostic device according to the present invention will be described with reference to the accompanying drawings.

FIG. 1 is a front view of an optical dental caries diagnostic device according to the present invention, wherein (a) of FIG. 1 shows the state in which the length of a body unit is increased and (b) of FIG. 1 shows the state in which the length of the body unit is decreased, and FIG. 2 is a front view of the optical dental caries diagnostic device according to the present invention, wherein (a) of FIG. 2 shows the state in which a light-emitting member is bent at a right angle and (b) of FIG. 2 shows the state in which the light-emitting member is bent at 45 degrees.

As shown in FIGS. 1 and 2, the optical dental caries diagnostic device according to the present invention includes a body unit 100 having a predetermined length, a light-emitting member 200 configured to radiate light having a predetermined wavelength band, a power supply unit 300 configured to supply electric power to the light-emitting member 200, and a filter unit 400 configured to allow only light having a specific wavelength band to selectively pass therethrough.

In the optical dental caries diagnostic device according to the present invention, the length of the body unit 100 is adjustable so as to be convenient during use thereof or during storage thereof. In particular, the light-emitting member 200 is configured to be turned at a predetermined angle from the body unit 100 in order to easily check whether an inside of each tooth, i.e. an inner surface of each tooth, is decayed.

FIG. 3 is an exploded perspective view of the optical dental caries diagnostic device according to the present invention, and FIG. 4 is an exploded perspective view of the body unit constituting the optical dental caries diagnostic device according to the present invention.

Referring to FIGS. 1 to 4, the length of the body unit 100 having the predetermined length is adjustable in a longitudinal direction thereof, and the body unit includes a first body 110, a second body 120, a connection member 130, and a control member 140.

Specifically, the first body 110, the interior of which is empty and the external shape of which approximately cylindrical shape, is provided in a circumferential surface thereof with a straight slit 111 having a predetermined length and width in a longitudinal direction thereof, the slit being configured to guide movement of a projecting portion 142 of the control member 140, a description of which will follow. In addition, one or more fixing recesses 111' having relatively widely incised surfaces are provided at opposite ends of the slit 111 and between the opposite ends of the slit. The fixing recesses are configured to limit movement of the projecting portion 142 at predetermined positions.

Furthermore, an indicator 112, such as a number or a special character, is located in the vicinity of the slit 111, more specifically near each fixing recess 111', such that the extent to which the light-emitting member 200 is bent can be easily recognized with the naked eye depending on the position of the projecting portion 142.

For example, it is assumed that "0" is engraved on a right end part of the slit 111, "1" is engraved on a middle part of the slit 111, and "2" is engraved on a left end part of the slit 111 as the indicators 112 and that the light-emitting member 200 is bendable at 45 degrees and 90 degrees. In the state in which the light-emitting member 200 is not bent at all, the projecting portion 142 is located in the fixing recess 111' located at the right end of the slit 111 (see (a) of FIG. 1). In the case in which the light-emitting member 200 is bent at a right angle, on the other hand, the projecting portion 142 is located in the fixing recess 111' located at the left end of the slit 111 (see (a) of FIG. 2). When the light-emitting member is bent at 45 degrees, the projecting portion 142 is located in the fixing recess 111' located at the middle of the slit 111.

Of course, the number of fixing recesses 111' provided in the slit 111 and the number of indicators 112 may be adjusted and changed without limit depending on the bending angle of the light-emitting member 200.

One end of the first body 110, which corresponds to the left side in the figures, is closed by a first sealed surface 113, whereas the other end of the first body is completely open.

A first through-hole 114, a second through-hole 115, and a first fastening protrusion 116 are provided at the first sealed surface 113. Here, the first through-hole 114 is configured to allow sliding movement of a hinge shaft 212, a description of which will follow, therethrough, the second through-hole 115 is configured to allow extension of a cable 310 therethrough, and the first fastening protrusion 116 is configured to connect the first body 110 and a lamp frame 210 to each other.

Next, the second body 120 will be described.

In the same manner as the first body 110, the second body 120 has an approximately cylindrical shape having an empty interior. However, the second body has a smaller inner diameter than the first body 110 so as to be received in the first body 110, and opposite ends of the second body are open.

A first flange 121 is provided at an outer side surface of an edge of one side (a left side in the figure) of the second body 120, and the first flange 121 is configured to prevent complete separation between the second body and the connection member 130 after assembly. Also, it is preferable for one or more first concavo-convex portions 122 to be provided at an outer side surface of an edge of the other side of the second body 120 so as to have a circular band shape in a circumferential direction thereof, and the first concavo-convex portions prevent slip when the second body 120 is pulled by hand in a state of being received in the first body 110.

The connection member 130, which connects the first body 110 and the second body 120 to each other, has an approximately cylindrical shape having an empty interior.

An outer side surface of the connection member 130 is fixed to an inner surface of an edge of the other side of the first body 110 in tight contact therewith, whereas an inner side surface of the connection member is located at the outer surface of the second body 120, and a second flange 131 is formed at an outer side surface of an edge of the other side of the connection member such that the connection member is prevented from being introduced into the first body 110.

When describing in brief a method of assembling the first body 110, the second body 120, and the connection member 130, the part of the second body 120 at which the first concavo-convex portions 122 are formed is penetrated through the connection member 130 from a left side thereof, and the connection member 130 is fixed to the first body 110 (see FIG. 4).

As a result, the second body 120 is freely movable into the connection member 130 and the first body 110, whereas the second body is prevented from being completely separated from the connection member 130 by the first flange 121.

The control member 140 configured to control turning of the light-emitting member 200 while being located in an inner space of an edge of one side of the first body 110 will be described.

The control member 140, which has a hollow cylindrical shape, includes an incised portion 141, a projecting portion 142, a second sealed surface 143, and a second fastening protrusion 144.

Specifically, the incised portion 141 is configured to provide a predetermined level or more of elastic force when the projecting portion 142 is pressed by the hand, and is located at an upper part of a circumferential surface of the control member 140 so as to be movable along the slit 111 when the control member 140 is received in the first body 110. Although three incised lines are at right angles to each other in the figure when viewed from above, change is possible as long as it is possible to achieve the same object, operation, and effect.

The projecting portion 142, which is a means configured to select the turning angle of the light-emitting member 200, is located at a center of the incised portion 141 constituted by the three incised lines located at right angles to each other, and is moved along the slit 111 of the first body 110. For example, in order to bend the light-emitting member 200 at 90 degrees, the projecting portion 142 is pushed forwards in a state of being pressed. On the other hand, in order to return the light-emitting member 200 to a straight shape thereof, the projecting portion 142 is pulled rearwards in a state of being pressed.

Of course, it is obvious that, when the force applied to the projection portion 142 is removed after the light-emitting member 200 reaches a desired position, the position of the light-emitting member 200 is fixed, since the projecting portion 142 is seated in the fixing recess 111'.

One end of the control member 140, which corresponds to a left side in the figure, is closed by the second sealed surface 143. The second fastening protrusion 144, which is connected to a hinge shaft 212, a description of which will follow, is provided on the second sealed surface 143, and a hole, through which the cable 310 extends, is formed in a center of the second sealed surface.

Next, the light-emitting member 200, which radiates light in order to recognize dental caries, will be described.

Healthy teeth and decayed teeth may be checked by radiating light having a predetermined wavelength band. That is, porphyrins, which are microbial metabolites of dental plaque, emit red fluorescence in a wavelength band of about 400 nm, which is called a Soret band, and therefore whether dental caries occur and the position of dental caries can be checked with the naked eye.

The light-emitting member 200, which performs the above-described function, is mounted to the body unit 100. More specifically, the light-emitting member includes a lamp frame 210 and a lamp 220 mounted to the lamp frame 210.

First, the lamp frame 210 has a cylindrical shape, and is located in front of the first sealed surface 113 of the first body 110. An incised groove 211 extending through a central point of a circle in a lateral direction of the lamp frame 210 while having a predetermined width and depth is formed in a rear surface of the lamp frame, i.e. in an end surface of one side of the lamp frame facing the first sealed surface 113.

A second fastening member 214 configured to fix the first fastening protrusion 116 of the first body 110 extends through the incised groove 211 such that the first body 110 and the lamp frame 210 are connected to each other. Here, the second fastening member 214 may be constituted by a bolt, configured to extend through the lamp frame 210 from a side surface thereof after the first fastening protrusion 116 is seated in the incised groove 211, and a nut; however, the present invention is not limited thereto.

In addition, a hinge shaft 212 having one side connected to the incised groove 211 and the other side connected to the second fastening protrusion 144 is provided such that the lamp frame 210 is turned at a predetermined angle from the first body 110, as previously described. Reference numeral 213 indicates a first fastening member configured to fix the other side of the hinge shaft 212 and the second fastening protrusion 144. The first fastening member may be constituted by a bolt and a nut; however, the first fastening member is not particularly restricted as long as it is possible to perform the same object and function.

Meanwhile, it is preferable for the lamp frame 210 to be provided at a predetermined position of an outer side surface thereof with a coupling groove 215 configured to allow a filter frame 410, a description of which will follow, to be detachably attached to the lamp frame therethrough.

Here, it is preferable for the lamp 220, which is mounted to the lamp frame 210, to be a light-emitting diode (LED) lamp capable of radiating light having a predetermined wavelength band, preferably visible light, more preferably light having a wavelength band of 405 to 450 nm, most preferably light having a wavelength band of 405 to 410 nm.

Next, the power supply unit 300, which supplies electric power to the lamp 220, will be described. In the present invention, the power supply unit 300 includes a cable 310 having a predetermined length and a connection terminal 320.

One side of the cable 310 is directly or indirectly connected to the lamp 220, and extends through the second through-hole 115 of the first body 110 and the control member 140 and is then exposed at a rear of the second body 120. The other side of the cable is connected to the connection terminal 320.

The connection terminal 320 may receive electric power from electronic devices, such as portable terminals, including mobile phones, laptop computers, and tablets, and desktop PCs. It is preferable for the connection terminal to receive electric power from portable terminals, such as mobile phones, laptop computers, and tablets. It is most preferable for the connection terminal to receive electric power from mobile phones, which are carried by many students, including most adults.

Here, it is obvious that the type of the connection terminal 320 may vary depending on the kinds or specifications of the portable terminals.

Although not shown in the drawings, it is obvious that a switch configured to control the supply of electric power to the lamp 220 even though the connection terminal 320 is connected to an electronic device may be further provided.

Finally, the filter unit 400, which is located in front of the light-emitting member 200 and which is detachably coupled to the light-emitting member 200, will be described.

The filter unit 400, which is configured to selectively transmit only light having a specific wavelength band, includes a filter frame 410 formed in a cylindrical shape having a predetermined length, the filter frame being provided at an outer side surface thereof with a second concavo-convex portion 411 configured to prevent slip when gripped by the hand, and an optical filter 420 mounted to the filter frame 410, the optical filter being configured to selectively transmit only light having a wavelength band of 405 to 410 nm.

When the wavelength band of the light radiated by the lamp 220 is wide to some extent, i.e. when the light is visible light having a wavelength band of 400 to 700 nm or light having a short wavelength band of 400 to 450 nm, it is difficult to accurately check whether red light, which appears when dental caries occur, exists due to blue light or green light. Of course, when a lamp configured to radiate only light having a wavelength band of 405 to 410 nm is used, it is possible to easily check red light. However, it is necessary to separately manufacture or purchase a lamp configured to radiate only light having a specific wavelength band; however, such a lamp is very expensive.

However, when a filter unit 400 having an optical filter 420 capable of selectively transmitting only light having a specific wavelength band in which red fluorescence clearly appears, e.g. a wavelength band of 405 to 410 nm, is mounted to the lamp frame 210, it is possible to accurately check whether dental caries occur even though the wavelength band of light that is radiated is wide to some extent, and therefore it is possible to reduce manufacturing cost.

Of course, after the filter unit 400 is separated from the lamp frame 210, the filter unit 400 may be brought in front of the eye such that only light having a specific wavelength band that has passed through the filter unit is transmitted to an optical cell. Even in this case, it is possible to obtain the same effect.

Meanwhile, the optical filter, which selectively transmits or does not selectively transmit light having a specific wavelength band, corresponds to well-known art, and therefore a detailed description thereof will be omitted.

Hereinafter, a method of determining dental caries using the optical dental caries diagnostic device according to the present invention will be described in brief.

First, the first body 110 and the second body 120 are extended so as to be easily held by the hand, and then the connection terminal 320 is connected to a mobile phone in the state in which the filter unit 400 is mounted to the lamp frame 210.

The light-emitting member 200 is adjusted so as to face teeth, and the light-emitting member is operated to radiate light. At this time, whether red fluorescence appears at some of the teeth is checked with the naked eye. Meanwhile, when an inner part of each tooth is checked, the projecting portion of the control member is pushed forwards to adjust the angle of the light-emitting member, and then whether dental caries occur and the position of dental caries may be checked in the same sequence as described above.

In the case in which the filter unit 400 is separated from the lamp frame 210, the filter unit 400 is brought in front of the eye, and whether red fluorescence appears is checked through the filter unit 400.

Although the specific details of the present invention have been described in detail, those skilled in the art will appreciate that the detailed description thereof discloses only preferred embodiments of the present invention and thus does not limit the scope of the present invention. Accordingly, those skilled in the art will appreciate that various changes and modifications are possible, without departing from the category and the technical idea of the present invention, and it will be obvious that such changes and modifications fall within the scope of the appended claims.

DESCRIPTION OF REFERENCE NUMERALS

100: Body unit
110: First body
111: Slit 111': Fixing recess
112: Indicator 113: First sealed surface
114: First through-hole 115: Second through-hole
116: First fastening protrusion
120: Second body
121: First flange 122: First concavo-convex portion
130: Connection member
131: Second flange
140: Control member
141: Incised portion 142: Projecting portion
143: Second sealed surface 144: Second fastening protrusion
200: Light-emitting member
210: Lamp frame
211: Incised groove 212: Hinge shaft
213: First fastening member 214: Second fastening member
215: Coupling groove
220: Lamp
300: Power supply unit
310: Cable
320: Connection terminal
400: Filter unit
410: Filter frame
411: Second concavo-convex portion
420: Optical filter

The invention claimed is:

1. An optical dental caries diagnostic device comprising:
a body unit;
a light-emitting member located in front of the body unit in one direction along a longitudinal direction, the light-emitting member being configured to radiate visible light; and
a power supply unit electrically connected to the light-emitting member, the power supply unit extending through the body unit and then being exposed at a rear of the body unit,
wherein a filter unit detachably coupled to the light-emitting member is provided in front of the light-emitting member in the one direction, and
wherein the body unit comprises:
a first body having a first sealed surface provided at an end of a first side of the first body, the first body having a hollow cylindrical shape;
a second body having a smaller inner diameter than an inner diameter of the first body, the second body being formed in a cylindrical shape having two open opposite ends and an empty interior;
a cylindrical connection member having an outer side surface disposed in contact with an inner side surface of a second side of the first body and an inner side surface located at an outer side surface of the second body; and
a control member located in an inner space of the first side of the first body, the control member being configured to control turning of the light-emitting member.

2. The optical dental caries diagnostic device according to claim 1, wherein the filter unit comprises:
a filter frame formed in a cylindrical shape having a predetermined length, the filter frame being provided at an outer side surface of the filter frame with a second concavo-convex portion; and
an optical filter mounted to the filter frame, the optical filter being configured to selectively transmit only light having a wavelength band of 405 to 410 nm.

3. The optical dental caries diagnostic device according to claim 2, wherein the light-emitting member is connected to the body unit so as to be turnable at a predetermined angle therefrom.

4. The optical dental caries diagnostic device according to claim 1, wherein a length of the body unit is adjustable in the longitudinal direction.

5. The optical dental caries diagnostic device according to claim 1,
   wherein the first body comprises: a slit formed in a circumferential surface thereof in the longitudinal direction thereof; an indicator provided in a vicinity of the slit; a first through-hole formed in the first sealed surface; a second through-hole formed in the first sealed surface; and a first fastening protrusion formed on an outside of the first sealed surface,
   wherein the second body comprises: a first flange provided at a circumferential surface of an edge of a first side thereof; and a first concavo-convex portion provided at a circumferential surface of an edge of a second side thereof,
   wherein the connection member comprises a second flange provided at a circumferential surface of an edge of a second side thereof,
   wherein the control member has a hollow cylindrical shape, the control member comprising: an incised portion provided at a predetermined position of a circumferential surface thereof; a projecting portion provided in a vicinity of the incised portion; and a second fastening protrusion provided at an end of a first side thereof so as to protrude therefrom by a predetermined length, and
   wherein the light-emitting member comprises: a lamp frame; and a lamp mounted to the lamp frame, the lamp frame having a cylindrical shape, the lamp frame being located in front of the first sealed surface of the first body in the one direction, the lamp frame comprising: an incised groove formed in an end surface thereof facing the first sealed surface, the incised groove extending through a central point thereof while having a predetermined width; a hinge shaft having one end connected to the incised groove and an opposite end connected to the second fastening protrusion; and a second fastening member configured to connect the first fastening protrusion of the first body and the lamp frame to each other.

6. The optical dental caries diagnostic device according to claim 5, wherein the lamp frame is provided at a predetermined position of an outer side surface thereof with a coupling groove configured to a filter frame.

7. The optical dental caries diagnostic device according to claim 1, wherein the power supply unit comprises:
   a cable having a predetermined length; and
   a connection terminal provided at one end of the cable, the connection terminal being of a type capable of being connected to a portable electronic device and a non-portable electronic device.

* * * * *